(12) United States Patent
Rawlinson et al.

(10) Patent No.: US 10,893,888 B2
(45) Date of Patent: Jan. 19, 2021

(54) SPINAL IMPLANT SYSTEM AND METHOD

(71) Applicant: Warsaw Orthopedic, Inc., Warsaw, IN (US)

(72) Inventors: Jeremy J. Rawlinson, Memphis, TN (US); Molly K. Rice, Memphis, TN (US); Jonathan Shultz, Coopersburg, PA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 16/401,957

(22) Filed: May 2, 2019

(65) Prior Publication Data

US 2020/0345397 A1    Nov. 5, 2020

(51) Int. Cl.
*A61B 17/70* (2006.01)
*A61B 17/88* (2006.01)

(52) U.S. Cl.
CPC ...... *A61B 17/7022* (2013.01); *A61B 17/7029* (2013.01); *A61B 17/7031* (2013.01); *A61B 17/7032* (2013.01)

(58) Field of Classification Search
CPC ............ A61B 17/7022; A61B 17/7029; A61B 17/7031; A61B 17/7032; A61B 17/7008; A61B 17/7004; A61B 17/701; A61B 17/8897; A61B 17/8869; A61B 17/3421; A61B 17/3468; A61B 17/7007; A61B 17/88; A61B 17/1757; A61B 17/02; A61B 17/3423; A61B 17/3439; A61B 17/3472; A61B 2017/00526; A61B 2017/00004; A61B 2017/00862; A61B 2017/0256; A61B 2090/064; A61B 2090/3989; A61B 2090/363; A61B 2090/3916
USPC .................................. 606/246–279, 300–328
See application file for complete search history.

(56) References Cited

U.S. PATENT DOCUMENTS

| | | | |
|---|---|---|---|
| 6,783,527 B2 | 8/2004 | Drewry et al. | |
| 8,328,849 B2* | 12/2012 | Nydegger | A61B 17/7022 606/254 |
| 8,641,736 B2* | 2/2014 | Marik | A61B 17/7032 606/263 |
| 9,055,979 B2* | 6/2015 | Alcock | A61B 17/7008 |
| 10,314,593 B2* | 6/2019 | Bardsley | A61B 17/12113 |
| 2005/0277922 A1* | 12/2005 | Trieu | A61B 17/7031 606/257 |

* cited by examiner

*Primary Examiner* — Pedro Philogene
(74) *Attorney, Agent, or Firm* — Sorell, Lenna & Schmidt, LLP

(57) ABSTRACT

A spinal construct comprises a member extending between a first end and a second end and includes a first layer and a second layer. The first layer includes a plurality of interlaced strands that define a first angle. The second layer includes a plurality of interlaced strands that define a second angle. The first angle is smaller than the second angle. Systems, implants, surgical instruments and methods are disclosed.

20 Claims, 6 Drawing Sheets

SPINAL IMPLANT SYSTEM AND METHOD

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods, bone screws and sub-laminar wire, for stabilization of a treated section of a spine. This disclosure describes an improvement over these prior technologies.

SUMMARY

In one embodiment, a spinal construct is provided. The spinal construct comprises a member extending between a first end and a second end and includes a first layer and a second layer. The first layer includes a plurality of interlaced strands that define a first angle. The second layer includes a plurality of interlaced strands that define a second angle. The first angle is smaller than the second angle. In some embodiments, systems, implants, surgical instruments and methods are disclosed.

In one embodiment, a vertebral tether is provided. The vertebral tether comprises an inner braid including a plurality of carriers oriented to define a first angle in a range of 15 through 65 degrees and 1 through 25 picks per inch. An outer braid includes a plurality of carriers oriented to define a second angle in a range of 35 through 90 degrees and 15 through 35 picks per inch.

In one embodiment, the spinal construct comprises an anterior tether extending between a first end and a second end. The tether comprises a first layer including a plurality of interlaced strands that define a first angle and a second layer including a plurality of interlaced strands that define a second angle. The first angle is smaller than the second angle. A bone fastener defines an implant cavity configured for disposal of the tether. A set screw has a penetrating element extending through at least a portion of the tether.

BRIEF DESCRIPTION OF THE DRAWINGS

The present disclosure will become more readily apparent from the specific description accompanied by the following drawings, in which.

DETAILED DESCRIPTION

Figure 1:
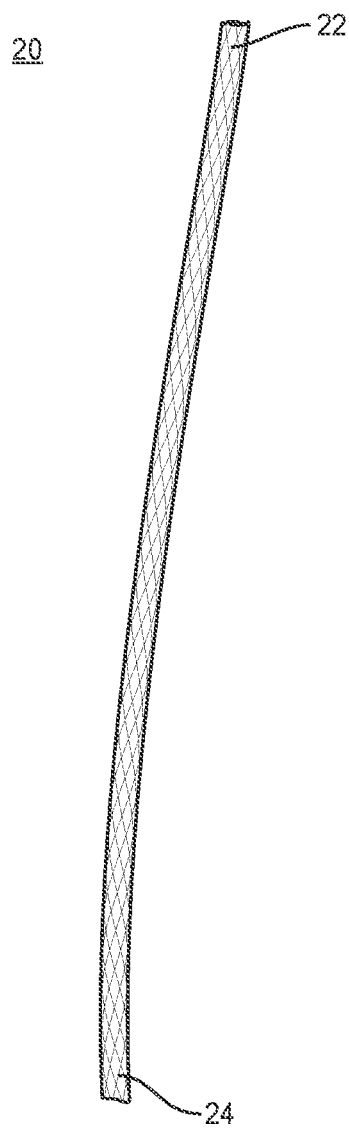
FIG. 1 is a side view of one embodiment of components of a surgical system in accordance with the principles of the present disclosure.

The exemplary embodiments of a surgical system and related methods of use are discussed in terms of medical devices for the treatment of musculoskeletal disorders and more particularly, in terms of a surgical system and method for correction of a spine disorder. In some embodiments, the surgical system may be employed in applications for correction of deformities, such as scoliosis and kyphosis.

In some embodiments, the present surgical system includes a spinal construct having a flexible tether. In some embodiments, the surgical system includes a spinal construct having an anterior tether. In some embodiments, the surgical system includes a spinal construct having a flexible tether to facilitate spinal correction with growth modulation.

In some embodiments, the present surgical system is employed with a method including vertebral body tethering that is utilized to achieve growth modulation in a young patient with a scoliotic deformity. In some embodiments, the present surgical system is employed with a method including the step of applying compression to vertebral growth plates with a unilateral system on the anterior spine to decrease the growth on the convexity of the deformed curve. In some embodiments, the surgical system provides reduction to facilitate growth on the concave side to catch up and either limit the progression of the deformity and/or restore neutral alignment.

In some embodiments, the present surgical system includes a tether having various parameters required to achieve a flexible tether that does not inhibit the natural movement of the spine while maintaining vertebral compression as a unilateral, tension-only band. In some embodiments, the tether includes a textile material, such as, for example, a braided construct with high-strength and high-stiffness in the loading direction, and soft, low-friction flexibility in other directions. In some embodiments, the braided tether is configured to be securely captured in a vertebral bone screw having a selected set screw configuration. In some embodiments, the set screw is configured to provide an appropriate axial grip to resist and/or prevent translation of the flexible tether relative to the head of the bone screw.

In some embodiments, the present surgical system includes a spinal construct having a flexible tether, such as, for example, a tension band. In some embodiments, the tether is configured to achieve a certain extension under a specific load. In some embodiments, the tether includes a stiffness needed to achieve growth modulation, high-strength and stiffness in a loaded direction and soft, low-friction flexibility in other directions. In some embodiments, the tether is configured to provide a fusionless system for the treatment of idiopathic scoliosis in young patients.

In some embodiments, the present surgical system includes a spinal construct having a flexible tether. In some embodiments, the flexible tether includes a tension-only band. In some embodiments, the tether includes a specific extension under a load. In some embodiments, the tether is configured to achieve vertebral compression for growth modulation of growth plates. In some embodiments, the tether is configured with a high strength and a low friction.

In some embodiments, the tether is fabricated with an ultra-high molecular weight polyethylene (UHMWPE). In some embodiments, the tether is fabricated with a high modulus polyethylene (HMPE). In some embodiments, the tether is fabricated with a dual-layered braid. In some embodiments, the tether is fabricated with selected braid specifications. In some embodiments, the tether is fabricated with a low friction configuration.

In some embodiments, the tether is constructed with an overall tensile strength. In some embodiments, the tether is constructed with an increased bulk to facilitate capture of the tether with a bone screw. In some embodiments, the tether is configured to maintain a circular configuration for symmetric flexing under a bending force. In some embodiments, the tether is configured with a dual braid to improve an axial grip when the tether is under non-axial compression in a capture mechanism. In some embodiments, the tether includes a dual layered braid configured to achieve redundancy in tensile loading.

In some embodiments, the tether includes a range of picks per inch. In some embodiments, the tether includes a range of braid angles. In some embodiments, the tether includes a twist that is independent for fibers before braiding ends. In some embodiments, the tether is configured with specific parameters and textiles to achieve a mechanical function in connection with a spinal correction treatment. In some embodiments, the tether is configured to achieve minimal extension under a load. In some embodiments, the tether is configured with flexibility in non-axial loading with high stiffness and strength in axial loading. In some embodiments, the tether is configured as a tension band. In some embodiments, the tether includes a braid angle. In some embodiments, the braid angle is configured to measure change in the orientation of the fibers of the outer braid that cause compression of the inner braid and align tension. In some embodiments, the inner braid has a smaller braid angle than the outer braid.

In some embodiments, the present surgical system is employed for treatment with a pediatric spine having a selected growth range, for example, a pediatric spine that grows 2 to 3 millimeters per level per year. In some embodiments, the present surgical system includes a tether having a stiffness configured to maintain axial loading within a selected growth range. In some embodiments, the tether includes an inner braid layer having 32 strands. In some embodiments, the tether includes an outer layer having 32 strands. In some embodiments, the tether includes an inner braid layer having a bulk that retains a selected circular cross section of the tether.

In some embodiments, the present surgical system includes a tether configured for engagement with a bone screw. In some embodiments, a portion of the bone screw is configured to penetrate the tether. In some embodiments, the tether is configured for a low friction separation to facilitate piercing. In some embodiments, the tether is configured for bulk compression of round dual-braid layers. In some embodiments, the tether includes an increased axial grip. In some embodiments, the tether is configured with a tensile strength greater than or equal to 1400 N. In some embodiments, a slip or grip breakage may not constitute failure. In some embodiments, the tether includes elongation of less than or equal to 8% at a force application of 200 N.

In some embodiments, the present surgical system includes a tether having an outer layer with a carrier having 32 ends, such as, for example, strands. In some embodiments, the present surgical system includes a tether having an outer layer with carriers that cross over each other along the outer layer at approximately 25 picks per inch+/−6 picks. In some embodiments, the outer layer includes a braid angle of approximately 67 degrees+/−15 degrees. In some embodiments, the outer layer includes an outer diameter of 3.25 mm+/−0.5 mm.

In some embodiments, the present surgical system includes a tether having an inner layer with a carrier having 32 ends, such as, for example, strands. In some embodiments, the present surgical system includes a tether having an inner layer with carriers that cross over each other along the inner layer at approximately 10 picks per inch+/−4 picks. In some embodiments, the inner layer includes a braid angle of approximately 40 degrees+/−15 degrees.

In some embodiments, the present surgical system is used with surgical navigation, such as, for example, fluoroscope or image guidance. In one embodiment, one or all of the components of the surgical system are disposable, peel-pack, pre-packed sterile devices. One or all of the components of the surgical system may be reusable. The surgical system may be configured as a kit with multiple sized and configured components.

In one embodiment, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In one embodiment, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about"

or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to exemplary embodiments of the present disclosure, which are illustrated in the accompanying figures. Turning to FIGS. 1-6, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 comprises a spinal construct 12 that includes a member, such as, for, example, a tether 20. In some embodiments, tether 20 is configured for disposal along an anterior portion of tissue forming a fusionless anterior construct. In some embodiments, tether 20 is configured with a selected extension under a load. In some embodiments, tether 20 is configured to achieve vertebral compression for growth modulation of a vertebral growth plate. Tether 20 is configured to facilitate vertebral growth modulation by limiting growth along a convex portion of vertebrae and allowing growth of a concave portion of vertebrae. Tether 20 is configured with an increased strength and stiffness in a loading direction, for example, in tension and decreased and low friction flexibility in other directions. Tether 20 is configured for engagement with a bone fastener 150, as described herein.

Figure 2:
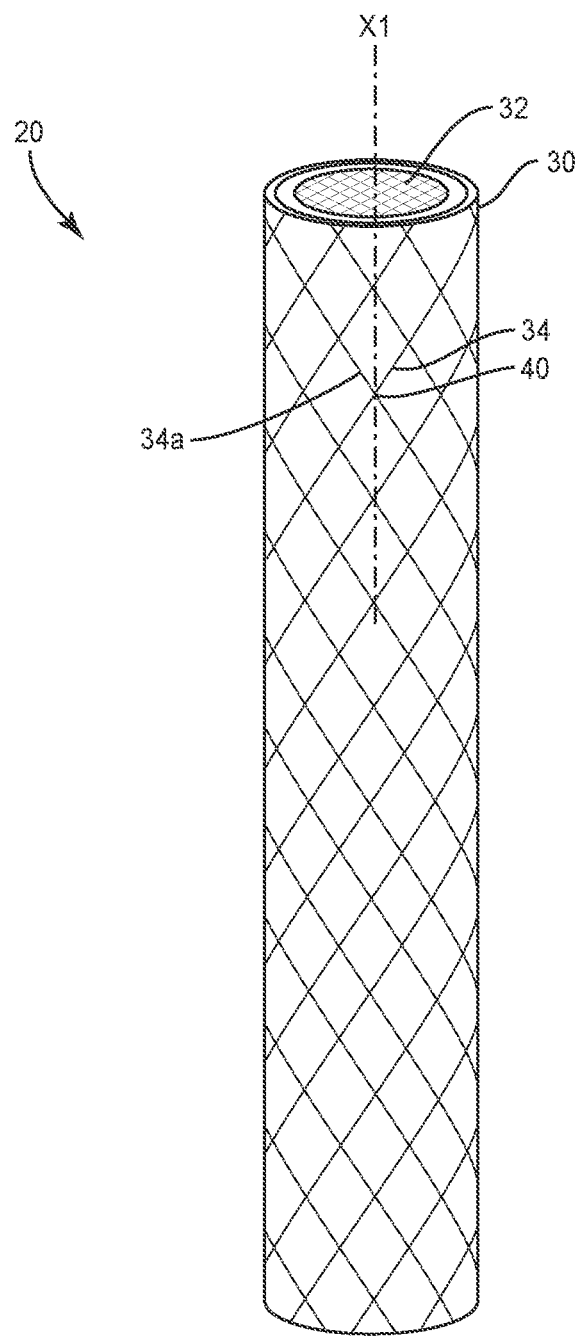
FIG. 2 is a perspective view of one embodiment of components of a surgical system in accordance with the principles of the present disclosure.

Tether 20 includes a flexible longitudinal element that extends between an end 22 and an end 24. Tether 20 includes a layer 30 and a layer 32. Layer 30 is configured for disposal about layer 32, as shown in FIG. 2. Layer 30 and layer 32 each comprise a braided cylindrical sleeve that defines an inner cavity. In some embodiments, layer 32 can include a mesh, textile network, solid or a non-hollow core. In some embodiments, layers 30, 32 can be relatively disposed in various orientations, such as, for example, co-axial, side by side, parallel, offset, intertwined, wrapped and/or staggered. Layers 30, 32 share a load applied to tether 20. In some embodiments, layer 32 provides strength and layer 30 provides a lubricious surface area. In some embodiments, layer 30 and/or layer 32 can include a smooth and lubricious surface. In some embodiments, layer 30 and/or layer 32 can be smooth, less friable and/or reduce micro-fraying in accordance with the material examples provided herein. In some embodiments, layer 30 and/or layer 32 can be manufactured from long-chain molecules of HMPE stretched along the length of each fiber.

Layer 30 includes a plurality of carriers 34. Carrier 34 is comprised of a plurality of ends, such as, for example, strands 36. Strands 36 are interlaced to form carrier 34. Strands 36 have a flexible configuration and may be fabricated from materials, such as, for example, UHMWPE, HMPE, fabric, silicone, polyurethane, silicone-polyurethane copolymers, polymeric rubbers, polyolefin rubbers, elastomers, rubbers, thermoplastic elastomers, thermoset elastomers and elastomeric composites. In some embodiments, carrier 34 includes a number of strands in a range of 1 through 100 strands. In some embodiments, carrier 34 includes 32 strands or ends. The configuration of carriers 34 and/or strands 36 includes various parameters to form tether 20.

For example, carriers 34 are disposed in a braided configuration, such as, for example, by interweaving carriers 34. Carriers 34 are braided in a configuration and apply a compressive force to layer 32 upon tensioning of tether 20, as described herein. Carrier 34 is interlaced with an adjacent carrier 34a at an intersection point, such as, for example, a pick 40, as shown in FIG. 2. In some embodiments, carriers 34 are oriented to define a number of picks 40 per square inch. Picks 40 define a number of carrier 34 crossing points per longitudinal inch. In some embodiments, tether 20 includes a selected number of picks 40 per square inch, for example, selected from a range of 15 through 35 picks per square inch. In some embodiments, tether 20 includes 25 picks 40 per square inch. In some embodiments, a selected number of picks 40 per square inch creates a lubricious surface area.

Carriers 34 are braided to form layer 30 and oriented relative to a longitudinal axis X1 of tether 20 to define a braid angle $\alpha$. In some embodiments, angle $\alpha$ is in a range of 35 through 90 degrees. In some embodiments, angle $\alpha$ is 67 degrees. In some embodiments, angle $\alpha$ is configured to measure a change in the orientation of carriers 34 that cause compression of the layer 32 and align tension.

Figure 3:
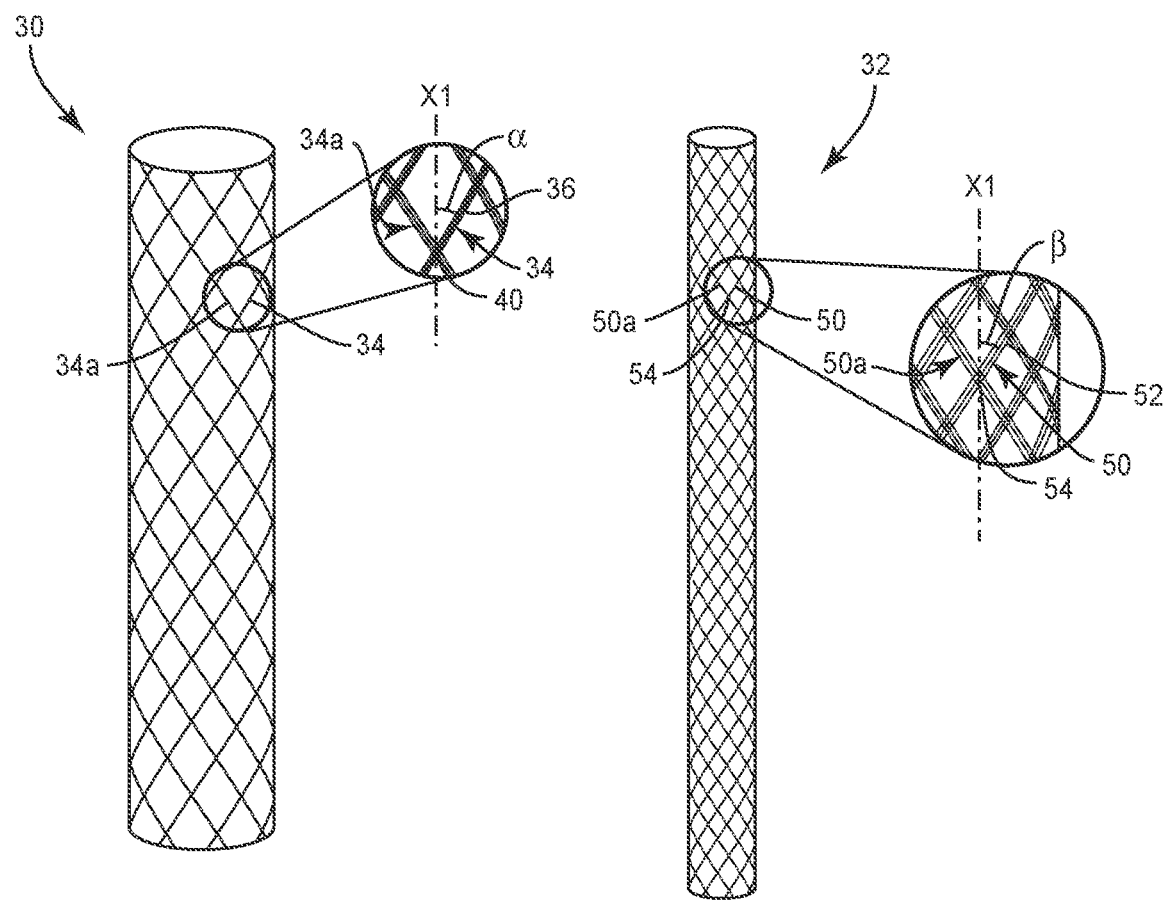
FIG. 3 is side view, with parts separated, of the components shown in FIG. 2.

Layer 32 includes a plurality of carriers 50. Carrier 50 is comprised of a plurality of ends, such as, for example, strands 52, as shown in FIG. 3. Strands 52 are interlaced to form carrier 50. Strands 52 have a flexible configuration and may be fabricated from materials, such as, for example, UHMWPE, HMPE, fabric, silicone, polyurethane, silicone-polyurethane copolymers, polymeric rubbers, polyolefin rubbers, elastomers, rubbers, thermoplastic elastomers, thermoset elastomers and elastomeric composites. In some embodiments, carrier 50 includes a number of strands in a range of 1 through 100 strands. In some embodiments, carrier 34 includes 32 strands or ends. The configuration of carriers 50 and/or strands 52 includes various parameters to form tether 20, as described herein.

For example, carriers 50 are disposed in a braided configuration, such as, for example, by interweaving carriers 50. Each carrier 50 is interlaced with an adjacent carrier 50a at an intersection point, such as, for example, a pick 54. In some embodiments, carriers 50 are oriented to define a number of picks 54 per square inch. Picks 54 define a number of carrier 50 crossing points per longitudinal inch. In some embodiments, tether 20 includes a selected number of picks 54 per square inch, for example, selected from a range of 1 through 25 picks per square inch. In some embodiments, tether 20 includes 10 picks 54 per square inch.

Carriers 50 are braided to form layer 32 and oriented relative to axis X1 to define a braid angle $\beta$. In some embodiments, angle $\beta$ is in a range of 15 through 65 degrees. In some embodiments, angle $\beta$ is 40 degrees. Angle $\beta$ is less than angle $\alpha$. In some embodiments, angle $\beta$ is less than angle $\alpha$ such that tether 20 achieves a selected extension under a selected load, and/or provides stiffness to achieve growth modulation, high-strength and stiffness in a loaded direction and soft, low-friction flexibility in other directions. In some embodiments, angle $\beta$ is equal to or greater than angle $\alpha$.

As an axial load is applied in tension to tether 20, carriers 34 compress to decrease angle $\alpha$. Carriers 34 compress layer 32 causing carriers 50 to compress and decrease angle $\beta$ such that layer 30 and layer 32 align in tension. Layers 30, 32 each include a selected and/or relative braid configuration having selected parameters, as described herein, such that tether 20 resists and/or prevents extension beyond a selected elongation under a selected load. As such, tether 20 includes a stiffness to achieve growth modulation, high-strength and stiffness in a loaded direction. Compression of layers 30, 32 under load causes tether 20 to sustain axial tension over time and resist and/or prevent creep of tether 20. The axial load is shared between layers 30, 32 to facilitate sustaining a tension on tether 20 during vertebral growth. In some embodiments, tether 20 is fabricated such that layers 30, 32 provide a selected tensile strength of tether 20, for example, the tensile strength of tether 20 being greater than or equal to 1400 N. In some embodiments, tether 20 includes an elongation at a selected force, for example, the elongation of tether 20 being 8% at a force of 200 N.

In some embodiments, the flexibility of tether 20 includes movement in a lateral or side to side direction and prevents expanding and/or extension in an axial direction upon tensioning and attachment with a targeted portion of an anatomy. In some embodiments, all or only a portion of tether 20 may have a semi-rigid, rigid or elastic configuration, and/or have elastic properties, similar to the material examples described above, such that tether 20 provides a selective amount of expansion and/or extension in an axial direction. In some embodiments, tether 20 may be compressible in an axial direction. Tether 20 can include a plurality of separately attachable or connectable portions or sections, such as bands or loops, or may be monolithically formed as a single continuous element.

Tether 20, layers 30, 32, one or more carriers 34, 52 and/or one or more strands thereof, can have a uniform thickness/diameter. In some embodiments, tether 20, layers 30, 32, one or more carriers 34, 52 and/or one or more strands thereof, may have various surface configurations, such as, for example, smooth and/or surface configurations to enhance fixation, such as, for example, rough, arcuate, undulating, porous, semi-porous, dimpled, polished and/or textured. In some embodiments, the thickness defined by tether 20, layers 30, 32, one or more carriers 34, 52 and/or one or more strands thereof, may be uniformly increasing or decreasing, or have alternate diameter dimensions along its length. In some embodiments, tether 20, layers 30, 32, one or more carriers 34, 52 and/or one or more strands thereof, may have various cross section configurations, such as, for example, oval, oblong, triangular, rectangular, square, polygonal, irregular, uniform, non-uniform, variable and/or tapered. In some embodiments, the surface of tether 20, layers 30, 32, one or more carriers 34, 52 and/or one or more strands thereof, may include engaging structures, such as, for example, barbs, raised elements and/or spikes to facilitate engagement with tissue of the targeted anatomy.

In some embodiments, tether 20, layers 30, 32, one or more carriers 34, 52 and/or one or more strands thereof, may have various lengths. In some embodiments, tether 20, layer 30 and/or layer 32 may include a length selected from a range of 600 through 900 mm. In some embodiments, tether 20, layer 30 and/or layer 32 may include a length of 750 mm. In some embodiments, tether 20, layer 30 and/or layer 32 may be braided, such as a rope, or include a plurality elongated elements to provide a predetermined force resistance. In one embodiment, all or only a portion of a tether 20 includes a coating. In some embodiments, the coating may include polyurethane, silicone-polyurethane copolymers, polymeric rubbers, polyolefin rubbers, elastomers, rubbers, thermoplastic elastomers, thermoset elastomers and/or elastomeric composites. In some embodiments, the coating includes visual indicia, such as, for example, coloration for identification during selection, a treatment and/or to facilitate manipulation.

Figure 4:
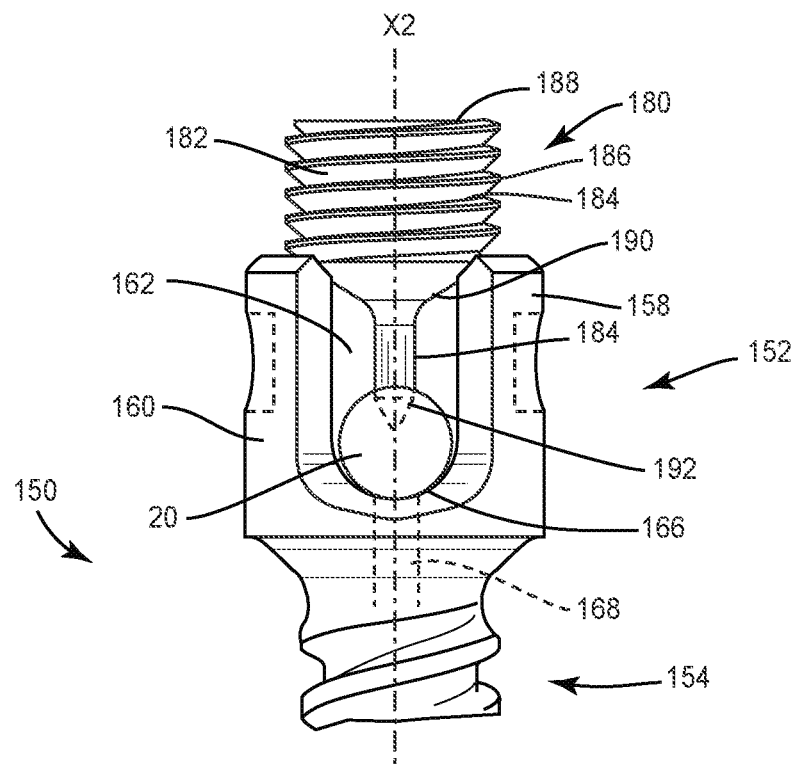
FIG. 4 is a side view, in part phantom, of one embodiment of components of a surgical system in accordance with the principles of the components of the present disclosure.
Figure 5:
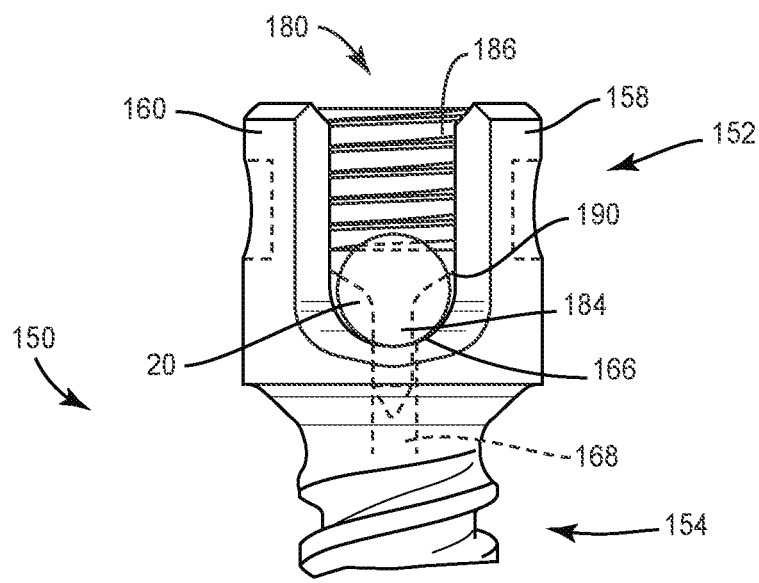
FIG. 5 is a side view, in part phantom, of components of one embodiment of components of a surgical system in accordance with the principles of the present disclosure.
Figure 6:
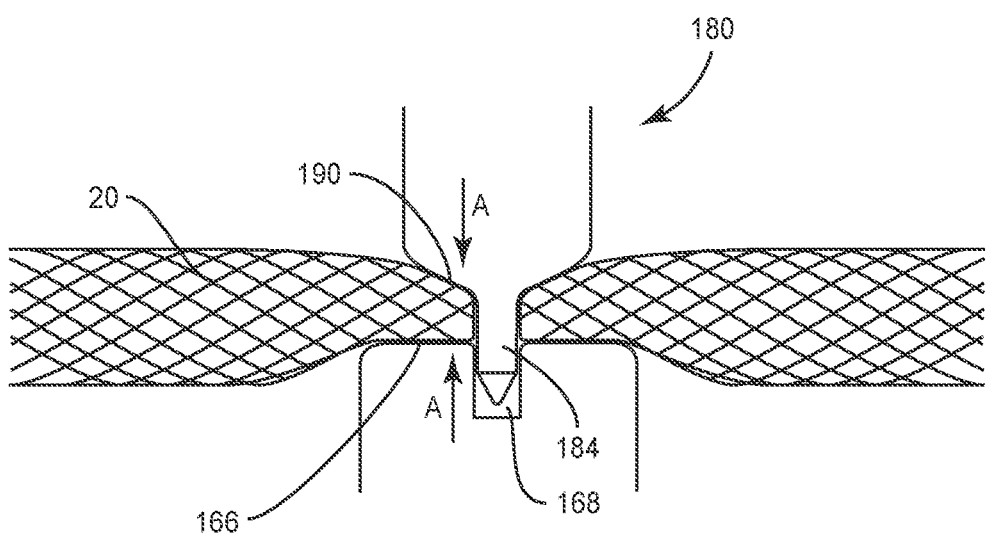
FIG. 6 is a cross section view of components one embodiment of components of a surgical system in accordance with the principles of the present disclosure.

Bone fastener 150 includes an implant receiver 152 and a screw shaft 154, as shown in FIGS. 4 and 5. Implant receiver 152 extends along and defines an axis X2. Implant receiver 152 includes a pair of spaced apart arms 158, 160 that define an implant cavity 162 therebetween configured for disposal of tether 20. Arms 158, 160 each extend parallel to axis X2. In some embodiments, arm 158 and/or arm 160 may be disposed at alternate orientations, relative to axis X2, such as, for example, transverse, perpendicular and/or other angular orientations such as acute or obtuse, coaxial and/or may be offset or staggered. Arms 158, 160 each include an arcuate outer surface extending between a pair of side surfaces. At least one of the outer surfaces and the side surfaces of arms 158, 160 have at least one recess or cavity therein configured to receive an insertion tool, compression instrument and/or instruments for inserting and tensioning bone fastener 150.

Cavity 162 is substantially U-shaped. In some embodiments, all or only a portion of cavity 162 may have alternate cross section configurations, such as, for example, closed, V-shaped, W-shaped, oval, oblong triangular, square, polygonal, irregular, uniform, non-uniform, offset, staggered, and/or tapered. Implant receiver 152 includes thread forms configured for engagement with a coupling member, such as, for example, a setscrew 180 to retain tether 20 within cavity 162, as described herein. In some embodiments, the inner surface of implant receiver 152 may be disposed with the coupling member in alternate fixation configurations, such as, for example, friction fit, pressure fit, locking protrusion/recess, locking keyway and/or adhesive. In some embodiments, all or only a portion of the inner surface of implant receiver 152 may have alternate surface configurations to enhance engagement with tether 20 and/or setscrew 180, such as, for example, rough, arcuate, undulating, mesh, porous, semi-porous, dimpled and/or textured. In some embodiments, implant receiver 152 may include alternate configurations, such as, for example, closed, open and/or side access.

Implant receiver 152 includes a surface, such as, for example, a bearing surface 166. Surface 166 defines a cavity, such as, for example, a cannulation 168. In some embodiments, cannulation 168 extends into all or a portion of screw shaft 154. Cannulation 168 is disposed in communication with cavity 162. Cannulation 168 is configured for disposal of all or a portion of a penetrating element 184, as described herein.

In some embodiments, implant receiver 152 is connectable with screw shaft 154 to include various configurations, such as, for example, a posted screw, a pedicle screw, a bolt, a bone screw for a lateral plate, an interbody screw, a uni-axial screw (UAS), a fixed angle screw (FAS), a multi-axial screw (MAS), a side loading screw, a sagittal adjusting screw (SAS), a transverse sagittal adjusting screw (TSAS), an awl tip (ATS), a dual rod multi-axial screw (DRMAS), midline lumbar fusion screw and/or a sacral bone screw.

Set screw 180 has a plug body 182 with an elongate member engaging portion, such as, for example, penetrating element 184 extending distally from plug body 182. Plug body 182 includes a surface 184 that defines a thread form 186. Thread form 186 is formed circumferentially about plug body 182. Plug body 182 includes a cavity, such as, for example, a socket 188 configured for engagement with a surgical instrument, such as, for example, a driver. The driver is configured to apply a driving force to set screw 180 to engage set screw 180 with implant receiver 152. Set screw 180 includes a lower bearing surface 190 which bears against tether 20 positioned between bone fastener 150 and set screw 180. Penetrating element 184 includes a distal end 192 tapered to facilitate penetration of penetrating element 184 into tether 20.

In use, attachment of tether 20 to bone fastener 150 with set screw 180 includes positioning tether 20 within cavity 162 against or adjacent bearing surface 166. Set screw 180 is aligned with an opening between arms 158, 160. Distal end 192 of penetrating element 184 contacts or partially penetrates tether 20 such that tether 20, layers 30, 32, one or more carriers 34, 52 and/or one or more strands thereof, are separated and/or compressed. Set screw 180 is advanced by its threads into implant receiver 152 until bearing surface 190 contacts tether 20 and crimps tether 20 between bearing surface 190 and bearing surface 166, and penetrating element 184 extends completely through tether 20.

Tether 20 has a reduced cross-sectional area along its crimped portion between bearing surfaces 190, 166. Penetrating element 184 is at least partially received in cannulation 168 of bone fastener 150, allowing complete penetration of tether 20 by penetrating element 184 in combination with crimping. Penetrating element 184 and/or bearing surfaces 166, 190 provide a bearing member against which tether 20 acts as it is tensioned or compressed with longitudinal forces, as shown by arrows A in FIG. 6. Penetrating element 184 facilitates axial grip of tether 20 such that translation of tether 20 relative to bone fastener 150 is resisted and/or prevented by friction generated between tether 20 and bearing surfaces 190, 166 and by the bearing support provided by penetrating element 184.

In assembly, operation and use, spinal implant system 10, similar to the systems and methods described herein, is employed with a surgical procedure, such as, for example, a correction treatment of an affected portion of a spine, for example, a correction treatment to treat adolescent idiopathic scoliosis and/or Scheuermann's kyphosis of a spine. In some embodiments, one or all of the components of spinal implant system 10 can be delivered or implanted as a pre-assembled device or can be assembled in situ. Spinal implant system 10 may be completely or partially revised, removed or replaced.

Figure 7:
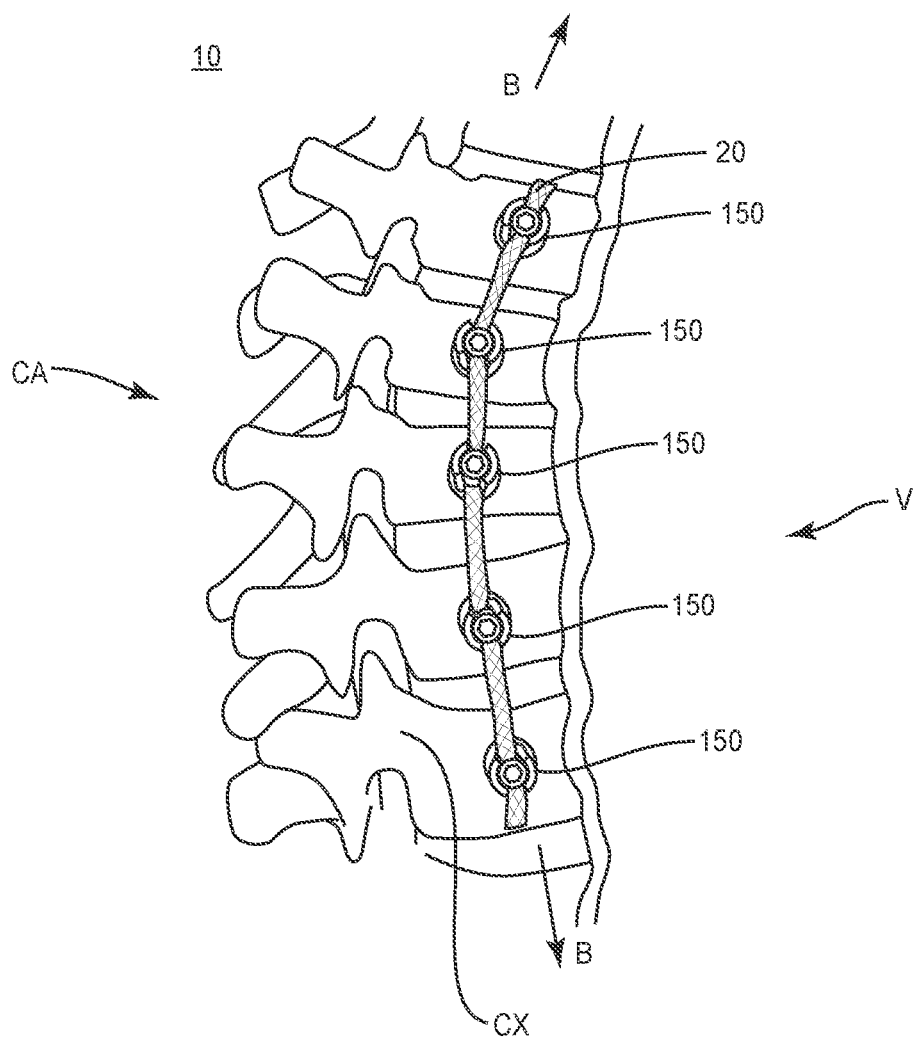
FIG. 7 is a plan view of one embodiment of components of a surgical system in accordance with the principles of the present disclosure disposed with vertebrae.

In use, to treat a selected section of vertebrae V, as shown in FIG. 7, a medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae V as well as for aspiration and irrigation of a surgical region. Pilot holes (not shown) are made in selected levels of vertebrae V for receiving one or more bone fasteners 150.

Tether 20 is disposed along vertebrae V and is positioned within cavities 162 of bone fasteners 150 against or adjacent bearing surfaces 166. Set screws 180 are aligned with the openings between arms 158, 160. For each bone fastener 150, distal end 192 of penetrating element 184 contacts or partially penetrates tether 20 such that tether 20, layers 30, 32, one or more carriers 34, 52 and/or one or more strands thereof are separated and/or compressed. Set screw 180 is advanced by its threads into implant receiver 152 until bearing surface 190 contacts tether 20 and crimps tether 20 between bearing surface 190 and bearing surface 166, and penetrating element 184 extends completely through tether 20.

Penetrating element 184 is at least partially received in cannulation 168 of bone fastener 150, allowing complete penetration of tether 20 by penetrating element 184 in combination with crimping tether 20. Penetrating element 184 facilitates axial grip of tether 20 such that translation of tether 20 relative to bone fastener 150 is resisted and/or prevented by friction generated between tether 20 and bearing surfaces 190, 166 and by the bearing support provided by penetrating element 184.

Tether 20 and/or a tension thereof is employed to displace, pull, twist or align vertebrae V as part of a correction system and treatment. In some embodiments, tether 20 has a flexible configuration, which includes movement in a lateral or side to side direction and resists and/or prevents expanding and/or extension in an axial direction upon fixation with vertebrae V. Tether 20 includes layer 30 comprising a braided sleeve with layer 32 comprising a braided sleeve disposed within an inner cavity of layer 30, as described herein.

For example, during vertebral growth of vertebrae V, an axial load is applied in tension to tether 20 such that carriers 34 compress to decrease angle α. Carriers 34 compress layer 32 causing carriers 50 to compress and decrease angle β such that layer 30 and layer 32 align in tension. Layers 30, 32 each include a selected and/or relative braid configuration having selected parameters, as described herein, such that tether 20 resists and/or prevents extension beyond a selected elongation under a load applied to tether 20 by vertebrae V during growth, as shown by arrows B in FIG. 7. As such, tether 20 includes a stiffness to achieve growth modulation, high-strength and stiffness in a loaded direction, as shown by arrows B in FIG. 7. The constant tension along tether 20 facilitates growth modulation by compressing vertebral growth plates along an anterior portion of vertebrae V. Growth along a convex CX portion of vertebrae V is decreased allowing growth of the concave CA portion of vertebrae V.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of bone fasteners 150 with vertebrae V. In some embodiments, the agent may include one or a plurality of therapeutic agents and/or pharmacological agents for release, including sustained release, to treat, for example, pain, inflammation and degeneration.

In some embodiments, the components of spinal implant system 10 may be employed to treat progressive idiopathic scoliosis with or without sagittal deformity in either infantile or juvenile patients, including but not limited to prepubescent children, adolescents with continued growth potential, and/or older children whose growth spurt is late or who otherwise retain growth potential. In some embodiments, the components of spinal implant system 10 may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
   a member extending between a first end and a second end and including a first layer and a second layer,
   the first layer including a plurality of interlaced strands that define a first angle, and
   the second layer including a plurality of interlaced strands that define a second angle,
   the first angle being smaller than the second angle,
   wherein the member has the same physical characteristics along the entire length of the member.

2. A spinal construct as recited in claim 1, wherein the member comprises an anterior tether.

3. A spinal construct as recited in claim 1, wherein the interlaced strands are braided.

4. A spinal construct as recited in claim 1, wherein at least one of the layers is fabricated from UHMWPE.

5. A spinal construct as recited in claim 1, wherein the first layer comprises a braid having a plurality of carriers including the interlaced strands, the carriers being oriented to define the first angle in a range of 15 through 65 degrees.

6. A spinal construct as recited in claim 5, wherein the second layer comprises a braid having a plurality of carriers including the interlaced strands, the carriers being oriented to define the second angle in a range of 35 through 90 degrees.

7. A spinal construct as recited in claim 1, wherein the first layer comprises a braid having a plurality of carriers including the interlaced strands, the carriers being oriented to define the first angle of 40 degrees.

8. A spinal construct as recited in claim 7, wherein the second layer comprises a braid having a plurality of carriers including the interlaced strands, the carriers being oriented to define the second angle of 67 degrees.

9. A spinal construct as recited in claim 1, wherein the first layer comprises a braid having a plurality of carriers including the interlaced strands, the carriers being oriented to define 1 through 25 picks per inch.

10. A spinal construct as recited in claim 9, wherein the second layer comprises a braid having a plurality of carriers including the interlaced strands, the carriers being oriented to define 15 through 35 picks per inch.

11. A spinal construct as recited in claim 1, wherein the first layer comprises a braid having a plurality of carriers including the interlaced strands, each carrier including 25 through 40 strands.

12. A spinal construct as recited in claim 11, wherein the second layer comprises a braid having a plurality of carriers including the interlaced strands, each carrier including 25 through 40 strands.

13. A spinal construct as recited in claim 1, wherein the member includes a tensile strength of greater than or equal to 1400 N.

14. A spinal construct as recited in claim 1, wherein the member includes an elongation of less than or equal to 8% at a force application of 200 N.

15. A spinal construct as recited in claim 1, further comprising a bone fastener defining an implant cavity configured for disposal of the member and a coupling member having a penetrating element extending through at least a portion of the member.

16. A vertebral tether comprising:
an inner braid including a plurality of carriers oriented to define a first angle in a range of 15 through 65 degrees and 1 through 25 picks per inch; and
an outer braid including a plurality of carriers oriented to define a second angle in a range of 35 through 90 degrees and 15 through 35 picks per inch,
wherein the tether has the same physical characteristics along the entire length of the tether.

17. A spinal construct comprising:
an anterior tether extending between a first end and a second end, the tether comprising a first layer including a plurality of interlaced strands that define a first angle and a second layer including a plurality of interlaced strands that define a second angle, the first angle being smaller than the second angle;
a bone fastener defining an implant cavity configured for disposal of the tether; and
a set screw having a penetrating element extending through at least a portion of the tether,
wherein the tether has the same physical characteristics along the entire length of the tether.

18. A spinal construct as recited in claim 17, wherein the first layer includes a plurality of carriers oriented to define a first angle in a range of 15 through 65 degrees and 1 through 25 picks per inch, and the second layer includes a plurality of carriers oriented to define a second angle in a range of 35 through 90 degrees and 15 through 35 picks per inch.

19. A spinal construct as recited in claim 17, wherein tether includes a tensile strength of greater than or equal to 1400 N.

20. A spinal construct as recited in claim 17, wherein the tether includes an elongation of less than or equal to 8% at a force application of 200 N.

* * * * *